United States Patent [19]

Sundeen et al.

[11] 4,235,885
[45] Nov. 25, 1980

[54] INHIBITORS OF MAMMALIAN COLLAGENASE

[75] Inventors: Joseph E. Sundeen, Yardley, Pa.; Tamara Dejneka, Skillman, N.J.

[73] Assignee: E. R. Squibb & Sons, Inc., Princeton, N.J.

[21] Appl. No.: 51,915

[22] Filed: Jun. 25, 1979

[51] Int. Cl.³ .................. A61K 37/00; A01N 37/00; A01N 37/30
[52] U.S. Cl. .................. 424/177; 424/319; 424/315; 424/320; 260/112.5 R
[58] Field of Search .............. 424/319, 315, 320, 177; 260/112.5 R

[56] References Cited
U.S. PATENT DOCUMENTS

| | | | |
|---|---|---|---|
| 4,053,651 | 10/1977 | Ondetti et al. | 424/319 |
| 4,105,776 | 8/1978 | Ondetti et al. | 424/274 |
| 4,179,434 | 12/1979 | Ondetti et al. | 260/112.5 R |

*Primary Examiner*—Delbert R. Phillips
*Assistant Examiner*—Blondel Hazel
*Attorney, Agent, or Firm*—Lawrence S. Levinson; Donald J. Barrack

[57] ABSTRACT

Mammalian collagenase is inhibited by compounds having the formula

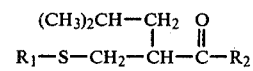

and salts thereof, wherein
$R_1$ is hydrogen or alkanoyl of 2 to 10 carbon atoms;
$R_2$ is hydroxy, amino, or

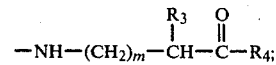

$R_3$ is hydrogen, alkyl of 1 to 4 carbon atoms,

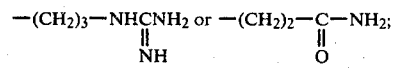

$R_4$ is hydroxy, amino, arginine, leucine, glutamine, alanine or glycine; and
m is 0 or an integer of 1 to 9.

25 Claims, No Drawings

INHIBITORS OF MAMMALIAN COLLAGENASE

RELATED APPLICATION

U.S. patent application Ser. No. 25,701, filed Apr. 2, 1979 by Ondetti and Pluscec, discloses mercaptoacyl-dipeptides that are ACE inhibitors; i.e., in mammals, they inhibit the action of angiotensin converting enzyme on angiotensin I, reducing the formation of angiotensin II. Angiotensin II has been implicated as a causative factor in various forms of hypertension in mammals. The application discloses compounds having the formula

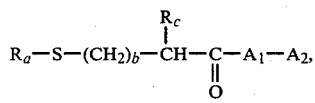

wherein $R_a$ can be, inter alia, hydrogen or alkanoyl; b is 0 or 1, $R_c$ can be, inter alia, alkyl of 1 to 7 carbon atoms; and $A_1$ and $A_2$ each is an α-amino or α-imino acid residue joined through a peptide bond.

BACKGROUND OF THE INVENTION

The patent and non-patent literature both contain disclosures of mercaptoacyl amido acid which are useful as ACE inhibitors (described above under "Related Application"). A representative disclosure is U.S. Pat. No. 4,053,651, which describes, inter alia, glycine derivatives having the formula

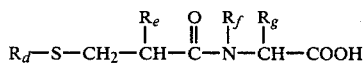

wherein $R_d$ can be, inter alia, hydrogen or alkanoyl; $R_e$ can be, inter alia, alkyl of 1 to 7 carbon atoms; and $R_f$ and $R_g$ can be, inter alia, hydrogen.

U.S. Pat. No. 4,105,776 also discloses mercaptoacy amino acids. In the disclosure of how to make the compounds of that invention intermediates are disclosed having the formulas

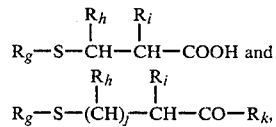

wherein, inter alia, $R_g$ can be hydrogen or alkanoyl; $R_h$ can be hydrogen; $R_i$ can be alkyl of 1 to 7 carbon atoms; $R_k$ can be amino; and j can be 0, 1 or 2.

BRIEF DESCRIPTION OF THE INVENTION

Mammalian collagenase is inhibited by compounds having the formula

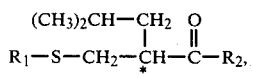

and salts thereof. In formula I, and throughout the specification, the symbols are as defined below.

$R_1$ is hydrogen or alkanoyl of 2 to 10 carbon atoms;
$R_2$ is hydroxy, amino, or

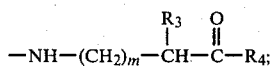

$R_3$ is hydrogen, alkyl of 1 to 4 carbon atoms,

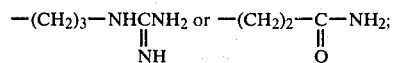

$R_4$ is hydroxy, amino, arginine, leucine, glutamine, alanine or glycine; and
m is 0 or an integer of 1 to 9.

DETAILED DESCRIPTION OF THE INVENTION

The compounds of formula I can be prepared using as a starting material 2-(hydroxymethyl)-4-methylpentanoic acid. Heating the starting material with phosphonic acid yields 4-methyl-2-methylenepentanoic acid which can in turn be reacted with a thio acid having the formula $$R_1'\text{-SH},\qquad\text{II}$$

wherein $R_1'$ is alkanoyl of 2 to 10 carbon atoms, to yield a product having the formula

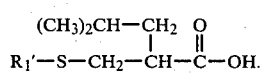

Treatment of a compound of formula III with concentrated ammonium hydroxide yields the ammonium salt of the mercapto acid having the formula

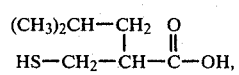

which can be neutralized with acid.

The products of formula III can also be used to prepare the products of formula I wherein $R_2$ is amino. Conversion of an acid of formula III to the corresponding amide having the formula

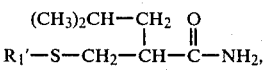

can be accomplished using conventional techniques. For example, the acid can be converted first to an acid halide, (e.g., by reaction with thionyl chloride) and subsequently to an amide by ammonolysis. If concentrated ammonium hydroxide is used for ammonlysis, the resulting product will be the mercapto product having the formula

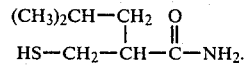

To prepare those compounds of formula I wherein $R_2$ is

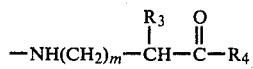

it is necessary to first convert the 2-(hydroxymethyl)-4-methylpentanoic acid starting material to the corresponding halogen substituted derivative having the formula

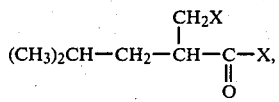

wherein X is a halogen atom, preferably chlorine or bromine. The conversion can be accomplished using, for example, a thionyl halide reagent.

Reaction of a compound of formula VII with an amino acid having the formula

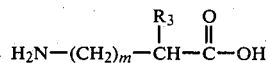

in the presence of alkali yields an intermediate having the formula

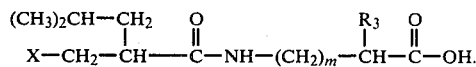

After the completion of the above reaction, but before isolation of the product, it is desirable to add more alkali to the reaction mixture to form a compound having the formula

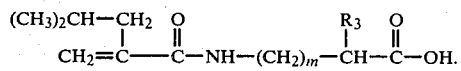

A compound of formula X can be reacted with a thio acid of formula II to yield a product having the formula

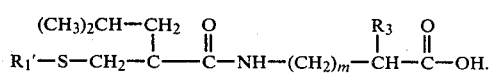

Treatment of a compound of formula XI with concentrated ammonium hydroxide yields an ammonium salt of the mercapto acid having the formula

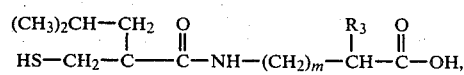

which can be neutralized with acid.

Those compounds of formula I wherein $R_2$ is

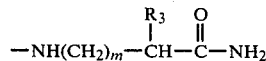

can be prepared from the corresponding carboxylic acid of formula X. The carboxylic acid is first converted to an acyl halide, preferably an acid chloride, using conventional techniques, e.g., reaction with a thionyl halide. The resulting acyl halide, i.e., a compound having the formula

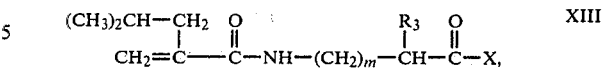

can be converted to the corresponding amide, i.e., a compound having the formula

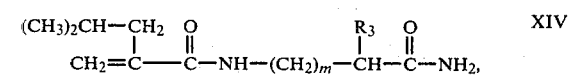

by ammonolysis. A compound of formula XIV can be reacted with a thio acid of formula II to yield a product having the formula

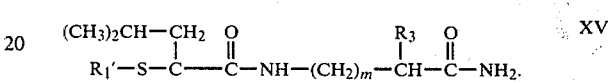

The corresponding mercapto compound having the formula

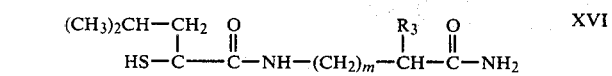

can be prepared by treating an alkanoylthio compound of formula XV with concentrated ammonium hydroxide.

Those compounds of formula I wherein $R_2$ is

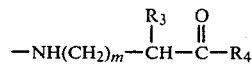

and $R_4$ is arginine, leucine, glutamine, alanine or glycine can be prepared from the corresponding carboxylic acid of formula XI. The carboxylic acid is first dissolved in an organic solvent, e.g., an aromatic hydrocarbon such as toluene, in the presence of an organic base. An alkyl halocarbonate such as ethyl chloroformate, is added to the solution and the solution of the resulting mixed anhydride is then mixed with an aqueous solution of the appropriate amino acid or amino acid salt (i.e., arginine leucine, glutamine, alanine or glycine) to yield the product having the formula

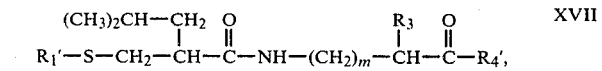

wherein $R_4'$ is arginine, leucine, glutamine, alanine or glycine. Treatment of a compound of formula XVII with concentrated ammonium hydroxide yields the corresponding mercapto compound having the formula

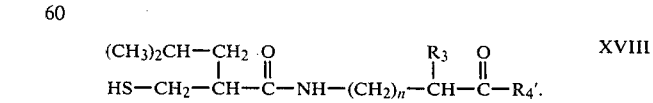

The compounds of this invention form basic salts with various inorganic and organic bases which are also within the scope of this invention. Such salts include ammonium salts, alkali metal salts, alkaline earth metal salts, salts with organic bases, e.g., dicyclohexylamine, benzathine, N-methyl-D-glucamine, hydrabamine and the like. The pharmaceutically acceptable salts are preferred, although other salts are also useful, e.g., in isolating or purifying the product.

The compounds of formula I have at least one asymmetric carbon atom; the carbon noted with an asterisk (*) in formula I. The compounds accordingly exist in stereomeric forms or in racemic mixtures thereof. All of these are within the scope of this invention. The above described synthesis can utilize the starting compounds in the form of a racemic mixture or as a stereomer. When $R_2$ is an amino acid or a dipeptide, the L-isomers with respect to the carbon atom of the amino acids is generally preferred.

In mammals, collagenase is one of the key enzymes involved in the cartilage and joint destruction of rheumatoid arthritis; see, for example, *Arthritis and Rheumatism*, 20 (6): 1231 (1977). It is, therefore, desirable to inhibit the action of the collagenase enzyme.

While not limiting the scope of this invention to a specific theory or mechanism of operation, it is nevertheless helpful to an understanding of the invention to review the possible reasons for the activity of the compounds of formula I. The main components of cartilage are the collagen polypeptide molecules. These polypeptides are cleaved by mammalian collagenase at a single site. The compounds of this invention resemble the susceptible sequence of the collagen molecules and, it is theorized, bind to the mammalian collagenase enzyme and inhibit its activity.

The mammalian collagenase enzyme contains zinc, which assists in the cleavage of a glycine-leucine or glycine-isoleucine bond and contains an extended cleft which interacts with an extended portion of the collagen molecule. This molecule in turn contains arginine as the last homologous amino acid in the substrate sequence adjacent to the cleavage site, a sequence showing a high degree of homology among the various types of collagen molecules. The inhibitors of this invention make use of these features of the enzyme and make modifications to enhance binding to the mammalian collagenase molecule.

The action of mammalian collagenase has also been implicated as a causative factor in several other diseases in mammals. These diseases include periodontal disease, corneal ulceration, tumor invasiveness, and epidermolysis bullosa; see, for example, *American Journal of Pathology*, 92 (2): 509 (1978) and *The New England Journal of Medicine*, 291 (13): 652 (1974).

For use in the treatment of rheumatoid arthritis, the compounds of this invention can be administered to a mammal in need thereof either orally or by injection intraarticularly into the affected joint. The daily dosage for a 70 kilogram mammal will be in the range of about 10 milligrams to 1 gram.

The compounds of this invention can be formulated in compositions such as tablets, capsules or elixirs for oral administration or in sterile solutions or suspensions for parenteral administration. About 10 to 500 mg of a compound of formula I or physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are specific embodiments of this invention.

EXAMPLE 1

2-(Mercaptomethyl)-4-methylpentanoic acid, ammonium salt (A) 4-Methyl-2-methylenepentanoic acid 4-Methyl-2-(methylhydroxy)pentanoic acid (8.7 g, see Example 3 below) is heated with 10 drops of 85% phosphonic acid in a Wood's metal bath at 220° C. for 20 minutes. A distillation head is attached and the pressure is slowly decreased to 60 mm while the temperature is increased to 270° C. Product starts to distill and the pressure is further decreased to 10 mm. The vapor temperature varies between 180° and 190° C. The yield of the title compound as distillate is 7.0 g.

(B) 2-[(Acetylthio)methyl]-4-methylpentanoic acid

The above compound 6.8 g is stirred with 5 ml of thiolacetic acid under argon for 5 days. It is concentrated in vacuo and a portion is distilled. The product boils at 117°–120° C. at 9 mm of Hg.

(C) 2-(Mercaptomethyl)-4-methylpentanoic acid, ammonium salt

The above product (0.8 g) is dissolved in 1.8 ml of concentrated ammonium hydroxide at 5° C. under argon and stirred at 5° C. for 2 hours. Product slowly crystallizes out. The reaction mixture is lyopholized to 0.8 ml and the product is filtered to yield 0.4 g of analytical sample. Solid liquifies at 120°–130° C. with ammonia given off.

Analysis calc'd for $C_7H_{17}O_2SN$: C, 46.90; H, 9.56; N, 7.81; S, 17.88. Found: C, 47.07; H, 9.73; N, 8.06; S, 17.45.

EXAMPLE 2

2-(Mercaptomethyl)-4-methylpentanamide (A) 2-[(Acetylthio)methyl]-4-methylpentanoyl chloride 2-[(Acetylthio)methyl]-4-methylpentanoic acid (6.0 g) is combined with thionyl chloride (5 ml). The reaction mixture is allowed to exotherm to 45° C. It is stirred at room temperature for about 16 hours and the acid chloride product is then vacuum distilled yielding 5.1 g, boiling point 80°–90° C. at 10 mm of Hg.

(B) 2-(Mercaptomethyl)-4-methylpentanamide

2-[(Acetylthio)methyl]-4-methylpentanoyl chloride (0.8 g) is cooled to 0° C. and the reaction flask is purged with argon. Concentrated ammonium hydroxide (2.5 ml) is added and the reaction mixture is stirred at room temperature under argon for 5 hours. The oily material slowly solidifies. Extraction with ethyl acetate yields 0.3 g of material which crystallizes upon standing for 16 hours under ethyl acetate yielding 0.2 g of the title compound, melting point 147°–154° C.

Analysis calc'd for $C_7H_{15}NOS$: C, 52.14; H, 9.37; N, 8.69; S, 19.88. Found: C, 52.18; H, 9.05; N, 8.40; S, 19.44.

EXAMPLE 3

N-[2-(Mercaptomethyl)-4-methyl-1-oxopentyl]glycine (A) Isocaproic Acid

Potassium cyanide (28 g) is partly dissolved in 125 ml of ethanol and 30 ml of water. Amyl bromide (63.6 g) is added and the reaction mixture is digested on the steam cone for 24 hours. The solution is decanted from the potassium bromide on to 35 g of potassium hydroxide. This is digested on the steam cone for 20 hours, diluted with 50 ml of water and concentrated in vacuo to remove the ethanol. A 1:1 mixture of sulfuric acid and water is added to the reaction mixture and product is extracted with petroleum ether to yield 60.6 g of crude product. Vacuum distillation yields 43.4 g of product boiling at 90°–98° C./9 mm of Hg.

(B) 2-(Hydroxymethyl)-4-methylvaleric acid

Diisopropylamine (20.6 g) is dissolved in 80 ml of dry tetrahydrofuran. This solution is cooled to −30° C. n-Butyllithium (77 ml of 2.6 M in hexane) is added dropwise in a nitrogen atmosphere at a rate that maintains the reaction at −30° to −20° C. This solution is stirred at −20° C. for 30 minutes. Isocaproic acid (11.6 g) in 10 ml of tetrahydrofuran is added dropwise at −20° to −10° C., then stirred at −10° C. for 30 minutes. In a separate flask, paraformaldehyde (28 g) is heated to about 200° C. and the vapors are carried in a stream of nitrogen over the surface of the tetrahydrofuran solution of the dilithium salt of isocaproic acid. During this procedure the temperature is kept between −10° and +10° C. After all of the paraformaldehyde has vaporized the reaction mixture is cooled to 0° C. and 10% hydrochloric acid is added dropwise until the reaction mixture becomes acidic. Product is extracted with 2 portions of ether (400 ml each). The ether is dried with magnesium sulfate, filtered and concentrated in vacuo to yield 13.2 g of crude material. Product is vacuum distilled to yield 9.0 g, boiling point 135°–142° C./9 mm of Hg.

(C) 2-(Chloromethyl)-4-methylvaleryl chloride

The above acid (9.0 g) is cooled to 0° C. Thionyl chloride (15 ml) is added dropwise. After addition the reaction mixture is stirred for about 16 hours. Product is distilled in vacuo to yield 6.8 g, boiling point 42°–50° C./9 mm of Hg.

(D) N-[(2-Chloromethyl)-4-methyl-1-oxopentyl]glycine

Glycine (2.0 g) is dissolved in 10 ml of water containing 1.1 g (0.027 mole) of sodium hydroxide. This solution is cooled to 5° C. and 15 ml of (1:3) toluene:tetrahydrofuran is added. The chloroacid chloride is dissolved in 20 ml of tetrahydrofuran and is added dropwise to the glycine solution at 5° C. The pH of the reaction mixture is monitered and maintained at pH 8 to 9 by the addition of an aqueous solution of 1.1 g of sodium hydroxide (volume 20 ml). After stirring for about 16 hours the aqueous layer is separated, washed with ether and acidified with 10% hydrochloric acid. Product is extracted with ethyl acetate, dried with magnesium sulfate, filtered and concentrated in vacuo to yield 6.0 g of product.

(E) N-(4-Methyl-2-methylene-1-oxopentyl)glycine

The above material is dissolved in 40 ml of 10% sodium hydroxide and digested on the steam cone for 1 hour. The reaction mixture is cooled, neutralized with 10% hydrochloric acid and product is extracted with chloroform. The chloroform is dried with magnesium sulfate, filtered and concentrated in vacuo. Product cyrstallizes to yield 4.3 g, melting point 73°–80° C.

(F) N-[2-[(Acetylthio)methyl]-4-methyl-1-oxopentyl]glycine

The above product is dissolved in 8 ml of thiolacetic acid and is stirred for about 16 hours under argon. The reaction mixture is concentrated in vacuo eliminating excess thiolacetic acid. Product (3.9 g) slowly crystallizes and is washed with hexane. Recrystallization from isopropyl ether-ethyl acetate yields an analytical sample, melting point 115°–122° C.

(G) N-[2-(Mercaptomethyl)-4-methyl-1-oxopentyl]glycine

The above product (0.3 g) is dissolved in 0.5 ml of concentrated ammonium hydroxide in a flask purged with argon. This solution is stirred at 5° C. for 20 minutes. The reaction mixture is treated with 10% hydrochloric acid to pH 2, and product is extracted with ethyl acetate. The ethyl acetate is dried with magnesium sulfate, filtered and concentrated in vacuo. A sample is dried at 60° C. in vacuo over potassium hydroxide and phosphorous pentoxide for 6 hours to yield the title compound.

Analysis calc'd for: $C_9H_{17}NO_3S$ C, 49.29; H, 7.81 N, 6.39; S, 14.62. Found: C, 49.44; H, 8.25; N, 6.51; S, 14.37.

EXAMPLE 4

N-[6-[2-[(Acetylthio)methyl]-4-methyl-1-oxopentyl]-1-oxohexyl]-L-arginine

(A) 6-[(4-Methyl-2-methylene-1-oxopentyl)amino]hexanoic acid, sodium salt 2-(Chloromethyl)-4-methylvaleryl chloride (6.73 g; see Example 3C) is dissolved in 100 ml of toluene and is cooled to 0° C. 6-Aminohexanoic acid is dissolved in 35 ml of 1 N sodium hydroxide and is added to the vigorously stirred toluene solution. After 2 hours, 75 ml of 1 N sodium hydroxide is added and the reaction mixture is stirred for about 16 hours. The toluene is decanted and the aqueous solution is acidified and extracted with ether. The ether is dried with magnesium sulfate, filtered and concentrated in vacuo to yield 6.7 g of product. From NMR this oil is shown to be a mixture of the chloro and dehydrohalogentated product. This is dissolved in 15 ml of 10% sodium hydroxide and digested on the steam cone for 1.5 hours. The aqueous solution is reacidified and extracted with ether. A sample (1.2 g) is removed and dissolved in 5 ml of 1 N sodium hydroxide. This solution is concentrated in vacuo and the residue is washed with ether. The solid is washed with cold ethyl acetate-ethanol and dried in vacuo to yield 1.0 g of product, melting point 166°–171° C. The product was found to contain ¼ mole of water.

(B) 6-[[2-[(Acetylthio)methyl]-4-methyl-1-oxopentyl]amino]hexanoic acid

The free acid of the above salt (1.9 g) is dissolved in 100 ml of benzene. Thiolacetic acid (0.76 g) is added and the solution is stirred under nitrogen for 48 hours. The reaction mixture is concentrated in vacuo and water is added to the pot residue. Product is extracted with ether and the ether is dried wth magnesium sulfate, filtered and concentrated in vacuo to yield 1.9 g of product.

(C)
N-[6-[2-[(Acetylthio)methyl]-4-methyl-1-oxopentyl]-1-oxohexyl]-L-arginine The above product (1.9 g) is dissolved in 150 ml of toluene and 0.66 g of triethylamine. This is cooled to 0° C. and 0.65 g of ethyl chloroformate is added dropwise. After addition the reaction mixture is stirred at 0° C. for 45 minutes and then filtered through Celite into a flask containing 1.02 g of L-arginine in 25 ml of water. This is stirred for 48 hours, and the aqueous layer is separated from the toluene and concentrated in vacuo to yield 1.9 g of crude product which is redissolved in water and chromatographed with water through 200 g of Avicel to remove unreacted arginine. After 500 ml of water has come through the column the product is eluted with 150 ml of water to yield 1.65 g of material. This is chromatographed through 200 g of LH-20 Sephadex. After 475 ml of water passed through the column, 10 ml fractions are collected. The chromatography is followed by spotting fractions on filter paper and developing colors for the two functional groups (guanidine and sulfhydryl). The first 6 fractions contain an impurity which gives a positive guanidine test but a negative S-acetyl. The S-acetyl is visualized by spraying with a 0.3% acetone solution of 2,2'-dithiobis-(5-nitropyridine) then converting it to the sulfhydryl group by passing the filter paper over $NH_3$ vapors. The subsequent fractions totalling 150 ml yield 1.0 g of desired product upon concentration in vacuo. (product softens 97°-120° C.). Analysis indicates the presence of 0.75 mole of water.

Analysis calc'd. for $C_{21}H_{39}N_5O_5S$.75 $H_2O$: C, 51.78; H, 8.40; N, 14.37; S, 6.58. Found: C, 51.70; H, 8.43; N, 14.60; S, 6.54.

EXAMPLE 5

N-[6-[[2-(Mercaptomethyl)-4-methyl-1-oxopentyl]amino]-1-oxohexyl]-L-arginine One gram of N-[6-[2-[(acetylthio)methyl]-4-methyl-1-oxopentyl]-1-oxohexyl-L-arginine (see Example 4) is dissolved in 3 ml of water. The solution is cooled to 5° C. and argon is passed over the solution. Concentrated ammonium hydroxide (1 ml) is added and the reaction mixture is stirred at 5° C. for 15 minutes. The solution is then lyophilized and the residue is stirred with acetonitrile (20 ml) containing 5 drops of water. The solid is filtered under argon and dried in vacuo over potassium hydroxide to yield 0.7 g of the title compound.

Analysis calc'd. for $C_{19}H_{37}N_5O_4S.H_2O$: C, 50.75; H, 8.74; N, 15.57; S, 7.12. Found: C, 50.96; H, 8.84; N, 15.98; S, 6.76.

EXAMPLE 6

6-[[2-[(Acetylthio)methyl]-4-methyl-1-oxopentyl]amino]hexanamide

(A) 6-[(4-Methyl-2-methylene-1-oxopentyl)amino]hexanamide

6-[(4-Methyl-2-methylene-1-oxopentyl)amino]hexanoic acid (2.8 g, see Example 4A) is cooled to 5° C. and thionyl chloride is added (5 ml). The reaction mixture is stirred at 35° C. for 3 hours, and concentrated in vacuo at room temperature to remove excess thionyl chloride. The pot residue is cooled to 5° C. and concentrated ammonium hydroxide (50 ml) is added and stirred for 1 hour. Product is extracted with ethyl acetate and the ethyl acetate solution is dried over magnesium sulfate, filtered and concentrated in vacuo. The resulting viscous oil slowly crystallizes, is washed with ether, and recrystallized from ethyl acetate to yield 0.8 g of the title compound, melting point 76°-82° C.

(B) 6-[[2-[(Acetylthio)methyl]-4-methyl-1-oxopentyl]amino]hexanamide

6-[(4-Methyl-2-methylene-1-oxopentyl)amino]hexanoic acid (0.7 g) is dissolved in 2 ml of thiolacetic acid and stirred under argon for 5 days. The sample is concentrated in vacuo, dissolved in ethyl acetate, and washed with water. The ethyl acetate solution is dried with magnesium sulfate in the presence of activated charcoal (to decolorize). Upon filtration and concentration in vacuo the product slowly crystallizes and is washed with hexane. The product has a melting point of 64°-80° C.

EXAMPLE 7

N-[N-[2-(Mercaptomethyl)-4-methyl-1-oxopentyl]-glycyl]-L-arginine

(A)
N-[2-[(Acetylthio)methyl]-4-methyl-1-oxopentyl]glycine, 4-nitrophenyl ester N-[2-[(Acetylthio)methyl]-4-methyl-1-oxopentyl]glycine (0.5 g) is dissolved in 30 ml of ethyl acetate along with p-nitrophenol (0.2 g). This solution is cooled to 5° C., N,N'-dicyclohexylcarbodiimide (0.4 g) is added portionwise and the reaction mixture is stirred at 5° for about 16 hours. The dicyclohexyl urea is filtered off and the filtrate is concentrated thoroughly in vacuo. Isopropyl ether is added to the residue and allowed to sit for about 16 hours. The crystalline solid is filtered to yield 0.4 g of product, melting point 95°-100° C.

(B)
N-[N-[2-[(Acetylthio)methyl]-4-methyl-1-oxopentyl]-glycyl]-L-arginine The above active ester (0.4 g) is dissolved in 50 ml of tetrahydrofuran (THF). This solution is cooled to 0° C., arginine (0.2 g) in 20 ml of water is added dropwise with vigorous stirring, and the reaction mixture is stirred for about 16 hours. It is concentrated in vacuo to 20 ml and the aqueous solution is washed with portions of ethyl acetate until the bright yellow color disappears from the aqueous phase. This is concentrated to 4 ml and chromatographed on 160 g of cellulose with 1:4 methanol:water. After 700 ml of solvent passes through the column, product elutes in 80 ml of solvent free of unreacted arginine. This is lyophilized to yield 0.4 g of analytical product containing 0.5 mole of water.

Analysis calc'd for $C_{17}H_{31}N_5O_5S.\frac{1}{2}H_2O$: C, 47.87; H, 7.56; N, 16.42; S. 7.5. Found: C, 48.09; H, 7.73; N, 16.47; S. 7.6.

(C)
N-[N-[2-(Mercaptomethyl)-4-methyl-1-oxopentyl]-glycyl]-L-arginine

The above product (0.4 g) is dissolved in 2 ml of water. The solution is purged with argon and cooled to 5° C. Concentrated ammonium hydroxide (1 ml) is added, the solution is stirred for 30 minutes and lyophilized for about 16 hours. Acetonitrile (10 ml) is added to the residue followed by 4 drops of water. This is stirred under argon until product becomes a colorless granular solid, which is filtered and dried in vacuo at 45° C. to yield 0.35 g of analytical sample, melting point 132°–146° C.

Analysis calc'd for $C_{15}H_{29}N_5O_4S$: C, 47.99; H, 7.79; N, 18.65; S, 8.54. Found: C, 47.55; H, 7.99; N, 18.34; S, 8.30.

EXAMPLE 8

N-[5-[[2-(Mercaptomethyl)-4-methyl-1-oxopentyl]amino]-1-oxopentyl]-L-arginine (A)

5-[[2-(Chloromethyl)-4-methyl-1-oxopentyl]amino]pentanoic acid

5-Aminovaleric acid (3.2 g) is dissolved in 15 ml of water containing 1.09 g of sodium hydroxide. This is cooled to 5° C. and 2-(chloromethyl)-4-methylvaleryl chloride in 30 ml of THF is added dropwise. The pH is maintained at 8–9 by the dropwise addition of 1.09 g sodium hydroxide in 20 ml of water as needed. After stirring for about 16 hours the reaction mixture is diluted with 30 ml of water and concentrated in vacuo to remove THF. The aqueous layer is washed with ether, and acidified with 10% hydrochloric acid. Product is extracted with ethyl acetate. The ethyl acetate is dried with magnesium sulfate, filtered and concentrated in vacuo to yield 4.3 g of product. Product is purified by the solvent system 500 parts ether: 10 parts methanol: 5 parts acetic acid, yielding 2.0 g of material.

(B)

5-[(2-Methylene-4-methyl-1-oxopentyl)amino]pentanoic acid

The above compound is dissolved in 10 ml of ethanol and 10 ml of 10% sodium hydroxide digested on the steam cone for 30 minutes, and concentrated in vacuo to a volume of 10 ml. This solution if neutralized with 10% hydrochloric acid and product is extracted with ethyl acetate. The ethyl acetate is dried with magnesium sulfate, filtered and concentrated in vacuo to yield 1.7 g of product.

(C)

5-[[2-[(Acetylthio)methyl]-4-methyl-1-oxopentyl]amino]pentanoic acid

The above material is dissolved in 3 ml of thiolacetic acid and stirred at room temperature for about 16 hours. The reaction mixture is washed with hexane and chromatographed on 100 g of silica using 50:5:2 ether:methanol:acetic acid, yielding 0.8 g of material.

(D)

5-[[2-[(Acetylthio)methyl]-4-methyl-1-oxopentyl]amino]pentanoic acid, 4-nitrophenyl ester The above material is dissolved in 10 ml of ethyl acetate along with p-nitrophenol (0.37 g), the solution is cooled to 5° C. and N,N-dicyclohexylcarbodiimide (0.54 g) is added portionwise. The reaction mixture is stirred at 5° C. for about 16 hours. Dicyclohexyl urea is filtered and the filtrate is concentrated in vacuo. The residue is dissolved in isopropyl ether and after standing for 2 hours it is filtered free of additional dicyclohexyl urea and concentrated in vacuo to yield 1.0 g of active ester as an oil.

(E)

N-[5-[[2-[(Acetylthio)methyl]-4-methyl-1-oxopentyl]amino]-1-oxopentyl]-L-arginine The above crude active ester is dissolved in 20 ml of THF, added to a 5 ml aqueous solution of arginine (0.4 g) and stirred at room temperature for about 16 hours. The reaction mixture is concentrated in vacuo to 5 ml and the aqueous solution is washed with ethyl acetate and chromatographed on 80 g of cellulose using 1:1 water:methanol. After 300 ml of solvent elutes through the column, clean product elutes in a 20 ml fraction. Further portions contained contaminated product. Yield 0.25 g of analytical sample.

Analysis calc'd for $C_{20}H_{37}N_5O_5S \cdot 1.7H_2O$: C, 48.82; H, 8.28; N, 14.23; S, 6.54. Found: C, 48.72; H, 8.24; N, 14.67; S, 6.99.

(F)

N-[5-[[2-(Mercaptomethyl)-4-methyl-1-oxopentyl]amino]-1-oxopentyl]-L-arginine

The above sample is dissolved in 1 ml of water cooled to 5° C. and purged with argon. Concentrated ammonium hydroxide (1 ml) is added, the reaction mixture is stirred at 5° C. for 30 minutes, lyophilized for about 16 hours and washed with 10 ml of acetonitrile containing 4 drops of water. Product is dried at 60° C. for 6 hours to yield an analytical sample melting point 117°–130° C.

Analysis calc'd for $C_{18}H_{35}N_5O_4S \cdot H_2O$: C, 49.63; H, 8.56; N, 16.08; S, 7.36. Found: C, 49.56; H, 8.44; N, 15.94; S, 7.77.

EXAMPLE 9

N-[8-[[2-(Mercaptomethyl)-4-methyl-1-oxopentyl]amino]-1-oxooctyl]-L-arginine (A)

8-[[2-(Chloromethyl)-4-methyl-1-oxopentyl]amino]octanoic acid

8-Amino caprylic acid (4.3 g) is dissolved in 20 ml of water containing 1.1 g of sodium hydroxide. To this is added 20 ml of THF, and 5 ml of toluene, and the solution is cooled to 5° C. 2-(Chloromethyl)-4-methylvaleryl chloride is dissolved in 10 ml of THF and added dropwise to the above solution. The pH of the reaction mixture is maintained between 8 and 9 during the reaction time by the addition of a total of 1.1 g of sodium hydroxide in 20 ml of water, as needed. After stirring at room temperature for about 16 hours, the aqueous layer is separated and acidified with 10% hydrochloric acid. Product is extracted with ethyl acetate and the ethyl acetate is dried with magnesium sulfate, filtered and concentrated in vacuo to yield 5.6 g of product.

(B)

8-[(2-Methylene-4-methyl-1-oxopentyl)amino]octanoic acid

The above product is dissolved in 40 ml of absolute ethanol and 40 ml of 10% sodium hydroxide, digested on the steam cone for 2 hours and cooled and acidified with 10% hydrochloric acid. Product is extracted with ethyl acetate and the solution is dried with magnesium sulfate, filtered and concentrated in vacuo to yield 4.8 g of the product. The above two reactions are repeated on the same scale to yield a total of 8.7 g of unsaturated product.

(C)

8-[[2-[(Acetylthio)methyl]-4-methyl-1-oxopentyl]amino]octanoic acid

The above product (8.2 g) is dissolved in 15 ml of thiolacetic acid, stirred under argon at room temperature for 48 hours, and concentrated in vacuo for 16 hours to remove excess thiolacetic acid. The residue is dissolved in ether and washed 4 times with water. The ether is dried with magnesium sulfate, filtered and concentrated in vacuo to yield 8.9 g. A small amount of impurity is washed away from the product with hexane. Yield 8.2 g.

(D)
8-[[2-[(Acetylthio)methyl]-4-methyl-1-oxopentyl-]amino]octanoic acid, 4-nitrophenyl ester The above compound (8.2 g) and p-nitrophenol (3.3 g) are dissolved in 200 ml of ethyl acetate and cooled to 5° C. N,N'-Dicyclohexylcarbodiimide (5.0 g) is added portionwise and the reaction mixture is stirred at 5° C. for about 16 hours. The dicyclohexylurea is filtered off and the ethyl acetate filtrate is concentrated in vacuo for 1 hour. Diisopropyl ether (4 ml) and ethyl acetate (4 ml) are added to the pot residue. A second crop of dicyclohexylurea is obtained. The filtrate is concentrated in vacuo to yield 8.7 g of crude active ester.

(E)
N-[8-[[2-[(Acetylthio)methyl]-4-methyl-1-oxopentyl-]amino]-1-oxooctyl]-L-arginine The active ester (4.4 g) is dissolved in 100 ml THF and added dropwise to a precooled solution of arginine (1.7 g) in 20 ml of water. This reaction mixture is stirred for about 16 hours, diluted with 350 ml of water and concentrated in vacuo to about 370 ml. This aqueous solution is washed with ethyl acetate until the bright yellow color disappears. During this procedure emulsion formation occurs which is broken up by the addition of diatomaceous earth to the separatory funnel. The aqueous layer is filtered and lyophilized. The crude residue (2.9 g) is chromatographed on 300 g of Avicel using 3:7 water:methanol. After 900 ml of solvent passes through the column, product elutes in 100 ml of solvent to yield 1.0 g of analytical sample after drying 6 hours at 50° C. in vacuo, melting point 85°–102° C. Product contains ½ molar equivalent of water.

Analysis calc'd for $C_{23}H_{13}N_5O_5S \cdot \frac{1}{2}H_2O$: C, 54.10; H, 8.68; N, 13.71; S, 6.28. Found: C, 54.36; H, 8.74; N, 13.46; S, 6.15.

(F)
N-[8-[[2-(Mercaptomethyl)-4-methyl-1-oxopentyl-]amino]-1-oxooctyl]-L-arginine Due to limited water solubility the above product (0.65 g) is first dissolved in 50 ml of argon purged ethanol followed by the addition of 2 ml of concentrated ammonium hydroxide. This reaction mixture is stirred for 1.5 hours at room temperature under argon. It is then lyophilized to almost dryness. Acetonitrile is added and the reaction mixture is stirred until product becomes granular and white. It is filtered and dried in vacuo at 50° C. to yield analytical sample, melting point 102°–130° C. Product contains ½ molar equivalent of water.

Analysis calc'd for $C_{21}H_{41}N_5O_4S \cdot \frac{1}{2}H_2O$: C, 53.82; H, 9.02; N, 14.91; S, 6.84. Found: C, 54.17; H, 9.15, N, 15.02; S, 6.60.

What is claimed is:

1. A method for reducing the adverse effects of mammalian collagenase in a mammalian host in need thereof, which comprises administering to said mammal an effective amount of a compound having the formula $$R_1-S-CH_2-\underset{\underset{CH_2CH(CH_3)_2}{|}}{CH}-\underset{\underset{O}{||}}{C}-R_2$$

or a salt thereof wherein $R_1$ is hydrogen or alkanoyl of 2 to 10 carbon atoms;
$R_2$ is hydroxy, amino or $$-NH-(CH_2)_m-\underset{\underset{R_3}{|}}{CH}-\underset{\underset{O}{||}}{C}-R_4;$$

$R_3$ is hydrogen, alkyl of 1 to 4 carbon atoms, $$-(CH_2)_3-\underset{\underset{NH}{||}}{NHCNH_2} \text{ or } -(CH_2)_2-\underset{\underset{O}{||}}{C}-NH_2;$$

$R_4$ is hydroxy, amino, arginine, leucine, glutamine, alanine or glycine; and
$m$ is 0 or an integer of 1 to 9.

2. A method in accordance with claim 1 wherein the mammalian host has rheumatoid arthritis.

3. A method in accordance with claim 1 wherein $R_1$ is hydrogen.

4. A method in accordance with claim 1 wherein $R_1$ is alkanoyl of 2 to 10 carbon atoms.

5. A method in accordance with claim 3 wherein $R_2$ is hydroxy.

6. A method in accordance with claim 3 wherein $R_2$ is amino.

7. A method in accordance with claim 3 wherein $R_2$ is $$-NH-(CH_2)_m-\underset{\underset{R_3}{|}}{CH}-\underset{\underset{O}{||}}{C}-R_4.$$

8. A method in accordance with claim 7 wherein $m$ is 0.

9. A method in accordance with claim 7 wherein $m$ is an integer of 1 to 9.

10. A method in accordance with claim 7 wherein $R_3$ is hydrogen.

11. A method in accordance with claim 7 wherein $R_3$ is alkyl of 1 to 4 carbon atoms.

12. A method in accordance with claim 7 wherein $R_3$ is $$-(CH_2)_3-\underset{\underset{NH}{||}}{NHCHN_2}.$$

13. A method in accordance with claim 7 wherein $R_3$ is $$-(CH_2)_2-\underset{\underset{O}{||}}{C}-NH_2.$$

14. A method in accordance with claim 3 wherein $R_4$ is hydroxy.

15. A method in accordance with claim 3 wherein $R_4$ is amino.

16. A method in accordance with claim 3 wherein $R_4$ is arginine, leucine, glutamine, alanine or glycine.

17. A method in accordance with claim 3 wherein the compound administered is 2-(mercaptomethyl)-4-methylpentanoic acid, ammonium salt.

18. A method in accordance with claim 3 wherein the compound administered is 2-(mercaptomethyl)-4-methylpentanamide.

19. A method in accordance with claim 3 wherein the compound administered is N-[2-(mercaptomethyl)-4-methyl-1-oxopentyl]glycine.

20. A method in accordance with claim 3 wherein the compound administered is N-[6-[2-[(acetylthio)methyl]-4-methyl-1-oxopentyl]-1-oxohexyl]-L-arginine.

21. A method in accordance with claim 3 wherein the compound administered is N-[6-[[2-(mercaptomethyl)]-4-methyl-1-oxopentyl]amino-1-oxohexyl]-L-arginine.

22. A method in accordance with claim 3 wherein the compound administered is 6-[[2-[(acetylthio)methyl]-4-methyl-1-oxopentyl]amino]hexanamide.

23. A method in accordance with claim 3 wherein the compound administered is N-[N-[2-(mercaptomethyl)-4-methyl-1-oxopentyl]glycyl]-L-arginine.

24. A method in accordance with claim 3 wherein the compound administered is N-[5-[[2-(mercaptomethyl)-4-methyl-1-oxopentyl]amino]-1-oxopentyl]-L-arginine.

25. A method in accordance with claim 3 wherein the compound administered is N-[8-[[2-(mercaptomethyl)-4-methyl-1-oxopentyl]amino]-1-oxooctyl]-L-arginine.

* * * * *

UNITED STATES PATENT OFFICE
CERTIFICATE OF CORRECTION

Patent No. 4,235,885         Dated November 25, 1980

Inventor(s) Joseph E. Sundeen, et al.

It is certified that error appears in the above-identified patent and that said Letters Patent are hereby corrected as shown below:

In column 1, line 28, "amino" is misspelled.
In column 1, line 41, "mercaptoacyl" is misspelled.
In column 11, line 25, the last sentence should read:
--Product is purified by chromatographing on 200 g of silica using as the solvent system 500 parts ether: 10 parts methanol: 5 parts acetic acid, yielding 2.0 g of material.--

Signed and Sealed this

Second Day of June 1981

[SEAL]

Attest:

RENE D. TEGTMEYER

Attesting Officer    Acting Commissioner of Patents and Trademarks